US010545061B1

(12) United States Patent
Xiao et al.

(10) Patent No.: US 10,545,061 B1
(45) Date of Patent: Jan. 28, 2020

(54) DECOUPLED DETERMINATION OF MAGNETOSTRICTION AND INVERSE MAGNETOSTRICTION

(71) Applicant: Ansys, Inc., Canonsburg, PA (US)

(72) Inventors: Yumin Xiao, Sewickley, PA (US); Ping Zhou, Bethel Park, PA (US); Ozgur Tuncer, Pittsburgh, PA (US)

(73) Assignee: Ansys, Inc., Canonsburg, PA (US)

( * ) Notice: Subject to any disclaimer, the term of this patent is extended or adjusted under 35 U.S.C. 154(b) by 338 days.

(21) Appl. No.: 15/679,497

(22) Filed: Aug. 17, 2017

Related U.S. Application Data

(60) Provisional application No. 62/376,861, filed on Aug. 18, 2016.

(51) Int. Cl.
| | |
|---|---|
| *G01L 3/10* | (2006.01) |
| *G01L 1/12* | (2006.01) |
| *G01R 33/18* | (2006.01) |
| *G01B 7/24* | (2006.01) |
| *G01L 5/00* | (2006.01) |

(Continued)

(52) U.S. Cl.
CPC ............ *G01L 3/102* (2013.01); *G01B 7/24* (2013.01); *G01L 1/125* (2013.01); *G01L 5/0023* (2013.01); *G01R 33/096* (2013.01); *G01R 33/18* (2013.01); *G01N 27/72* (2013.01); *G01R 33/0064* (2013.01); *G01R 33/1215* (2013.01); *G06F 17/50* (2013.01); *G06F 17/5009* (2013.01); *G06F 17/5018* (2013.01); *G06F 2217/16* (2013.01)

(58) Field of Classification Search
CPC ....... G01L 3/102; G01L 1/125; G01L 5/0023; G01R 33/18; G01R 33/096; G01R 33/0064; G01R 33/1215; G01R 33/02; G01B 7/24; G06F 17/5018; G06F 17/50; G06F 17/5009; G06F 2217/16; G01N 27/72

See application file for complete search history.

(56) References Cited

U.S. PATENT DOCUMENTS

| | | | | |
|---|---|---|---|---|
| 8,855,978 | B2* | 10/2014 | Uehara | G01R 33/0064 703/2 |
| 2013/0006593 | A1* | 1/2013 | Uehara | G01R 33/0064 703/2 |
| 2018/0188335 | A1* | 7/2018 | Tago | G06F 17/50 |

OTHER PUBLICATIONS

Lin et al., "A new nonlinear anisotropic model for soft magnetic materials", IEEE Transactions on Magnetics, vol. 42, Iss. 4, Apr. 2006, Published Mar. 20, 2006. (Year: 2006).*

* cited by examiner

*Primary Examiner* — Jonathan M Dunlap
(74) *Attorney, Agent, or Firm* — Jones Day

(57) ABSTRACT

Rapid calculation of magnetostriction effects can consist of calculating a stress field and a magnetic field in a structure by determining a magnetic field on the magnetic mesh, determining a magnetostriction from the magnetic field, applying the magnetostriction to the mechanical mesh, determining a stress field on the mechanical mesh, determining an inverse magnetostriction from the stress field, applying the inverse magnetostriction to the magnetic mesh, and determining a new magnetic field on the magnetic mesh by accounting for the inverse magnetostriction. Calculations can be based on data representing a structure, including a magnetic mesh, a mechanical mesh, and a plurality of material properties. After calculation is completed, data characterizing the calculated stress field and magnetic field for the structure can be provided as output. Related apparatus, systems, techniques, methods and articles are also described.

22 Claims, 7 Drawing Sheets

(51) Int. Cl.
  *G01R 33/09* (2006.01)
  *G01N 27/72* (2006.01)
  *G06F 17/50* (2006.01)
  *G01R 33/12* (2006.01)
  *G01R 33/00* (2006.01)

Coupled:

H: magnetic field
B: magnetic flux density
T: stress
S: strain $$\begin{bmatrix} B \\ S \end{bmatrix} = \begin{bmatrix} \mu & d \\ d^T & c \end{bmatrix} \begin{bmatrix} H \\ T \end{bmatrix}$$

*FIG. 2*

DECOUPLED DETERMINATION OF MAGNETOSTRICTION AND INVERSE MAGNETOSTRICTION

CROSS-REFERENCE TO RELATED APPLICATIONS

This application claims priority to U.S. Provisional Application No. 62/376,861, entitled "Decoupled Determination of Magnetostriction and Inverse Magnetostriction," filed Aug. 18, 2016, the entirety of which is herein incorporated by reference.

TECHNICAL FIELD

The subject matter described herein relates to more rapid and precise calculations to evaluate stress and magnetic fields in a presence of magnetostriction and inverse magnetostriction.

BACKGROUND

Magnetostriction and inverse magnetostriction are physical phenomena related to energy transformations. Magnetostriction represents a mechanical deformation of a body in response to the application of a magnetic field. Inverse magnetostriction represents a magnetic flux created when a body is mechanically deformed. Complex nature of these phenomena makes them difficult to predict with analytical models.

SUMMARY

In some variations, rapid calculation of magnetostriction effects can consist of calculating a stress field and a magnetic field in a structure by determining a magnetic field on the magnetic mesh, determining a magnetostriction from the magnetic field, applying the magnetostriction to the mechanical mesh, determining a stress field on the mechanical mesh, determining an inverse magnetostriction from the stress field, applying the inverse magnetostriction to the magnetic mesh, and determining a new magnetic field on the magnetic mesh by accounting for the inverse magnetostriction. In some variations, calculations can be based on data representing a structure, including a magnetic mesh, a mechanical mesh, and a plurality of material properties. After calculation is completed, in some variations, data characterizing the calculated stress field and magnetic field for the structure can be provided as output.

In some variations, material properties can include a magneto-mechanical coupling coefficient. In some variations, magneto-mechanical coupling coefficient can be dependent on the stress field. In some variations, determining the magnetic field can include mapping the stress field onto the magnetic mesh; and treating the stress field as a pre-stress. In some variations, determining the new magnetic field on the magnetic mesh can include reconstructing of a magnetic permeability to account for the inverse magnetostriction. In some variations, magnetic permeability can be isotropic before reconstructing. In some variations, magnetic permeability can become anisotropic after reconstructing.

In some variations, magnetic field and the stress field can change with time. In some variations, determining the magnetic field can include a calculation with a magnetic time constant. In some variations, determining the stress field can include a calculation with a stress time constant. In some variations, the magnetic time constant can be smaller than the stress time constant. In some variations, calculating step can be repeated until a converged solution is reached.

Non-transitory computer program products (i.e., physically embodied computer program products) are also described that store instructions, which when executed by one or more data processors of one or more computing systems, cause at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The subject matter described herein provides many technical advantages. These advantages include more accurate calculation results, faster run times for the calculations, ability to have separate meshes for the mechanical and magnetic domains, ability for experts in mechanics and magnetics to work on refinement of their respectful meshes and calculations separately. These advantages result in a better insight for the modeler.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 2 is a diagram illustrating a coupled approach to calculation of stress and magnetic fields in the presence of magnetostriction and inverse magnetostriction.

Like reference symbols in the various drawings indicate like elements.

DETAILED DESCRIPTION

Magnetostriction was first observed by J. Joule in 1842. It is typically described as a deformation of a structure as a result of its magnetization. The elongation or contraction in the direction of applied magnetic field is usually between $10^{-5}$ and $10^{-3}$ and is accompanied by the opposite sign deformation in the transverse direction, so that the volume remains almost the same.

Figure 1:
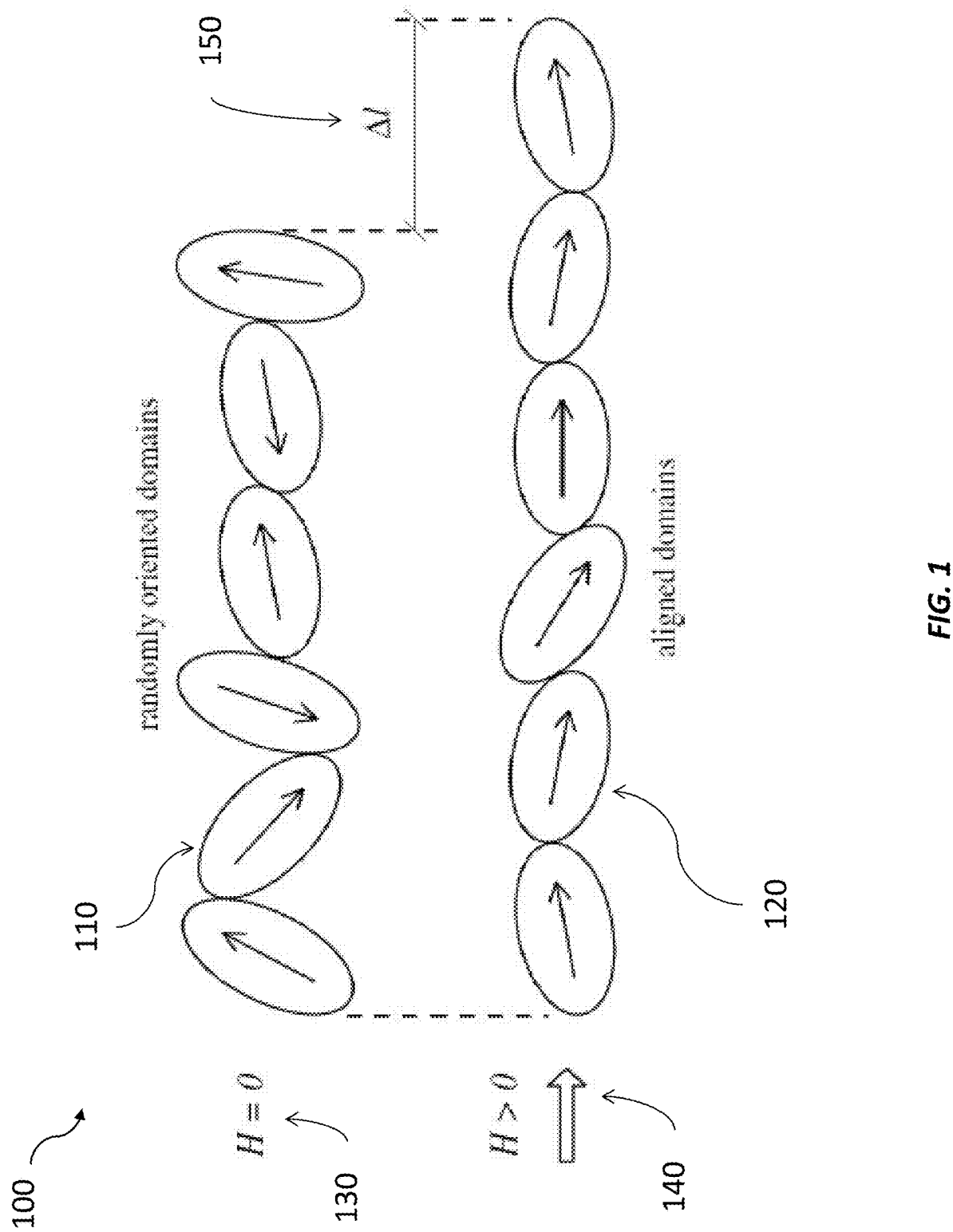
FIG. 1 is a diagram illustrating magnetostriction.

The phenomenon of magnetostriction can be regarded as an energy transformation from mechanical to magnetic and vice-versa. It can be described as a bidirectional magneto-mechanical coupling between the mechanical and magnetic fields in a magnetostrictive material. The origin of this phenomenon can be traced to the alignment of magnetic domains inside the material. FIG. 1 is an illustration of the magnetostriction effect simplified to one dimension. When no magnetic field is applied to the material (130), the series of domains 110 have randomly oriented magnetic moments. When a magnetic field is applied to the material (140), the series of domains (120) rotate to partially align themselves to the magnetic field direction resulting in a change in length Δl, 150. Applying a sufficiently high magnetic field 140 will result in perfectly aligned domains, in which case the material achieves the maximum magnetically induced strain (i.e. peak magnetostriction). Magnetostriction requires the magnetic domains to be longer in one dimension than the other two to obtain a change in length when the domain rotates. This, in general, results in anisotropy of the crystal structure of the material.

Magnetostriction is considered to be one of the main sources of noise in transformers. When an alternating voltage is applied to one or more windings of a transformer, a magnetic flux is generated in the transformer core laminations made of grain oriented electrical steel. The nonlinear anisotropic property of magnetostriction results in alternating changes of the core dimensions due to the varying magnetic flux in the laminations. Those magnetostrictive forces cause core vibrations which are transmitted to the tank via the insulation oil and the core clamping points. Part of the mechanical energy is eventually radiated by the tank walls as noise. In electric motors, magnetostrictive forces also contribute to motor vibration and noise.

Magnetostrictive materials convert energy between the mechanical and magnetic domains. They deform in response to applied magnetic fields and change their magnetic state when stressed. Some materials (such as Terfenol-D, Galfenol) have the ability to produce large magnetostrictive strains at moderate fields. Short response times (in the millisecond range) combined with resolutions on the order of microstrains make these materials well suited to precision sensing and actuation mechanisms.

Due to the complexity of the mechanism of magnetostriction, it is very difficult to calculate it accurately with analytical models. Empirical methods based on statistics and dimensional basic parameters are used by most transformer manufacturers and sensor producers. Those approaches present limitations when applied to new designs and do not enable accurate parametric studies. Therefore, prediction models based on finite element formulations will be utilized to describe accurately the complex interactions of the various design parameters and the coupling of the physical fields.

The finite element method (FEM) is widely used in engineering practice because it can model complex non-homogeneous and anisotropic materials and represent complicated geometry using the irregular grids. The FEM discretization produces a set of matrix differential equations. Because of the nonlinearity, the matrices generally are dependent of the solution vectors, so an iteration method such as Newton-Raphson method can be used to solve these nonlinear matrix equations. Namely, the nonlinear matrix equations are linearized for each nonlinear iteration. The linearized matrix equations may be solved by either a direct or iterative matrix solver.

The governing equation of magnetic field is given by:

$$\frac{1}{\rho}\frac{\partial A}{\partial t} + \nabla \times \left(\frac{\nabla \times A}{\mu}\right) = J \quad (1)$$

where t is time, A is the magnetic vector potential, ρ is the electrical resistivity, and μ is the magnetic permeability of material. J represents the current density. The magnetic flux density B can be expressed as:

$$B = \nabla \times A \quad (2)$$

The relationship between magnetic flux density B and magnetic field H is based on the constitutive law:

$$B = \mu H \quad (3)$$

For a discretized mechanical system, the governing equilibrium equation can be written as:

$$Cr + R_0 = R \quad (4)$$

where C is the system stiffness matrix, $R_0$ is the body force vector, and R the vector of external force, r is vector of node displacement. The strain-displacement relationship can be written as:

$$S = \nabla r \quad (5)$$

where S is the strain tensor. The stress-strain relationship can be described by:

$$T = CS \quad (6)$$

where T is the stress tensor, and C is the stiffness matrix.

When a magnetic field is applied to a magnetostrictive material, strain occurs within the material placed in a magnetic field in response to the flux density within the material, while the stress affects the magnetic field. For a coupled method 200 of FIG. 2, refer to:

$$\begin{bmatrix} B \\ S \end{bmatrix} = \begin{bmatrix} \mu & d \\ d^T & C^{-1} \end{bmatrix} \begin{bmatrix} H \\ T \end{bmatrix} \quad (7)$$

$$d^T = \frac{\partial \lambda}{\partial H}\bigg|_T \quad (8)$$

$$d = \frac{\partial B}{\partial T}\bigg|_H \quad (9)$$

where d and $d^T$ are magneto-mechanical coupling coefficients, and λ is magnetostriction induced by magnetic field H. In a coupled approach, the coupled equation 210 involves a matrix of material properties 220 and is solved for magnetic and stress fields 230. The magnetic field and mechanical stress field are solved together, which means both fields are solved on the same mesh simultaneously by using the same matrix solver.

Figure 3:
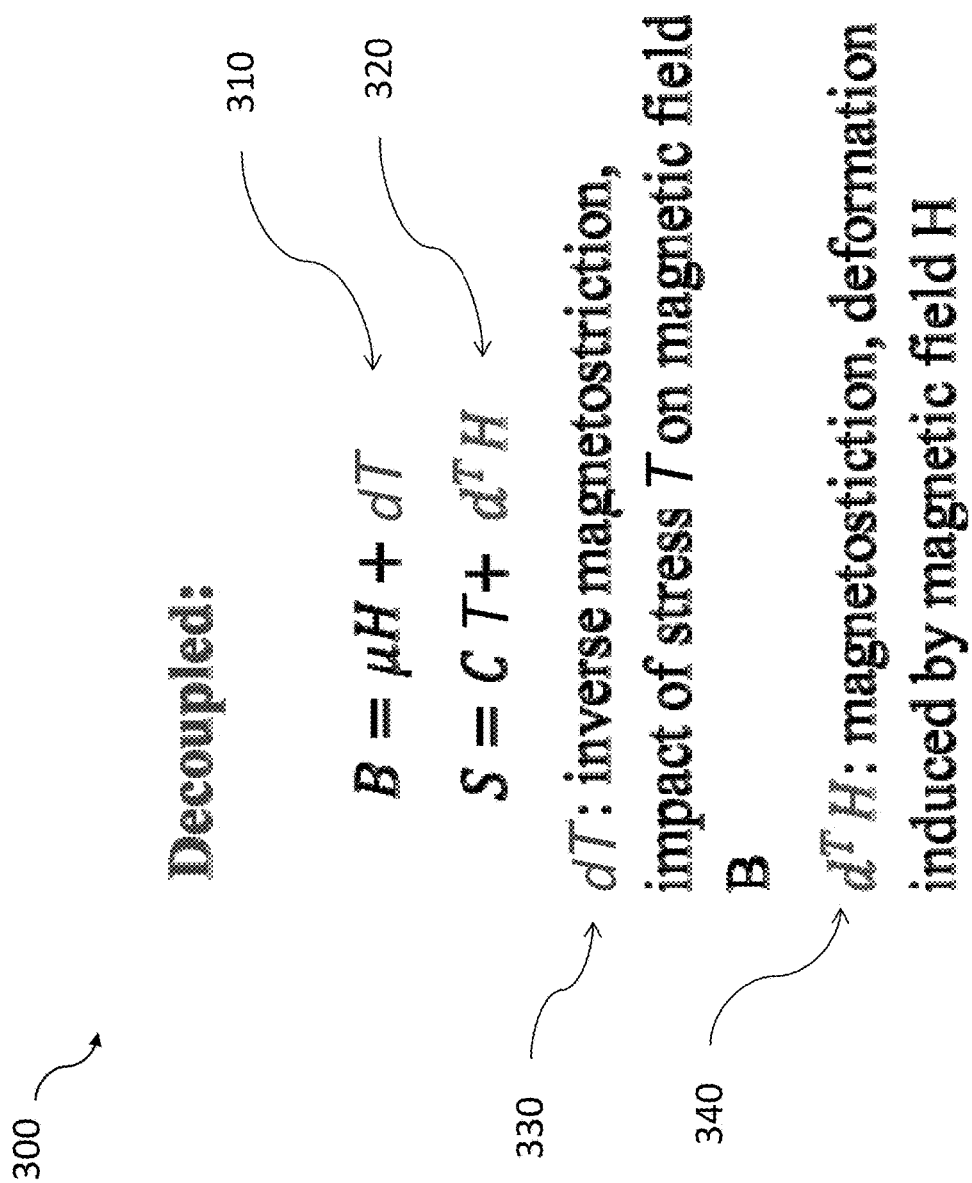
FIG. 3 is a diagram illustrating a decoupled approach to calculation of stress and magnetic fields in the presence of magnetostriction and inverse magnetostriction.

A decoupled method 300 is illustrated in FIG. 3. It offers flexibility for general multi-physics applications, because time constants in the electromagnetic field and in the mechanical field can differ significantly from each other. Time constant in the magnetic field can be less than one half of the time constant in the mechanical field, or less than one tenth, or less than one hundredth. For computational efficiency, the mesh density for properly capturing the corresponding physics can be different between the electromagnetic field simulation and the mechanical field simulation. In addition, a decoupled approach also makes the development of individual simulators more efficient, reliable and easier to use by experts in the different fields. Such independent simulators can be implemented across different computer hardware (e.g., using different data processors on a single computing systems, using distributed server systems, using different threads on a single processor computer system, distributed across multiple processors on a graphics processing unit) in series or, in a preferred implementation wholly or partially in parallel.

In the decoupled method 300, as the magnetostriction is unrelated to the stress, the magnetostriction can be determined once the magnetic field distribution is obtained from electro-magnetic simulation. As a result, based on the derived magnetostriction, which is further treated as an external load force, the elastic analysis can be simplified by finding the stress in terms of the external load force. The coupled equation 210 can be rewritten as two decoupled equations 310 and 320.

$$B = \mu H + dT \tag{10}$$

$$S = C^{-1}T + d^T H \tag{11}$$

where $d^T H$ is magnetostriction 340, which is deformation induced by magnetic field H, and $d\,T$ is inverse magnetostriction 330, which is impact of stress T on magnetic field B.

In some variations of the decoupled method 300, the magnetic field and stress field can be calculated independently with different meshes and different solvers. In some implementations, magnetostriction can be included in the calculations without including inverse magnetostriction. In addition or in the alternative, inverse magnetostriction can be included in the calculations without including magnetostriction. In some variations, both magnetostriction and inverse magnetostriction can be included in the calculations.

Figure 4:
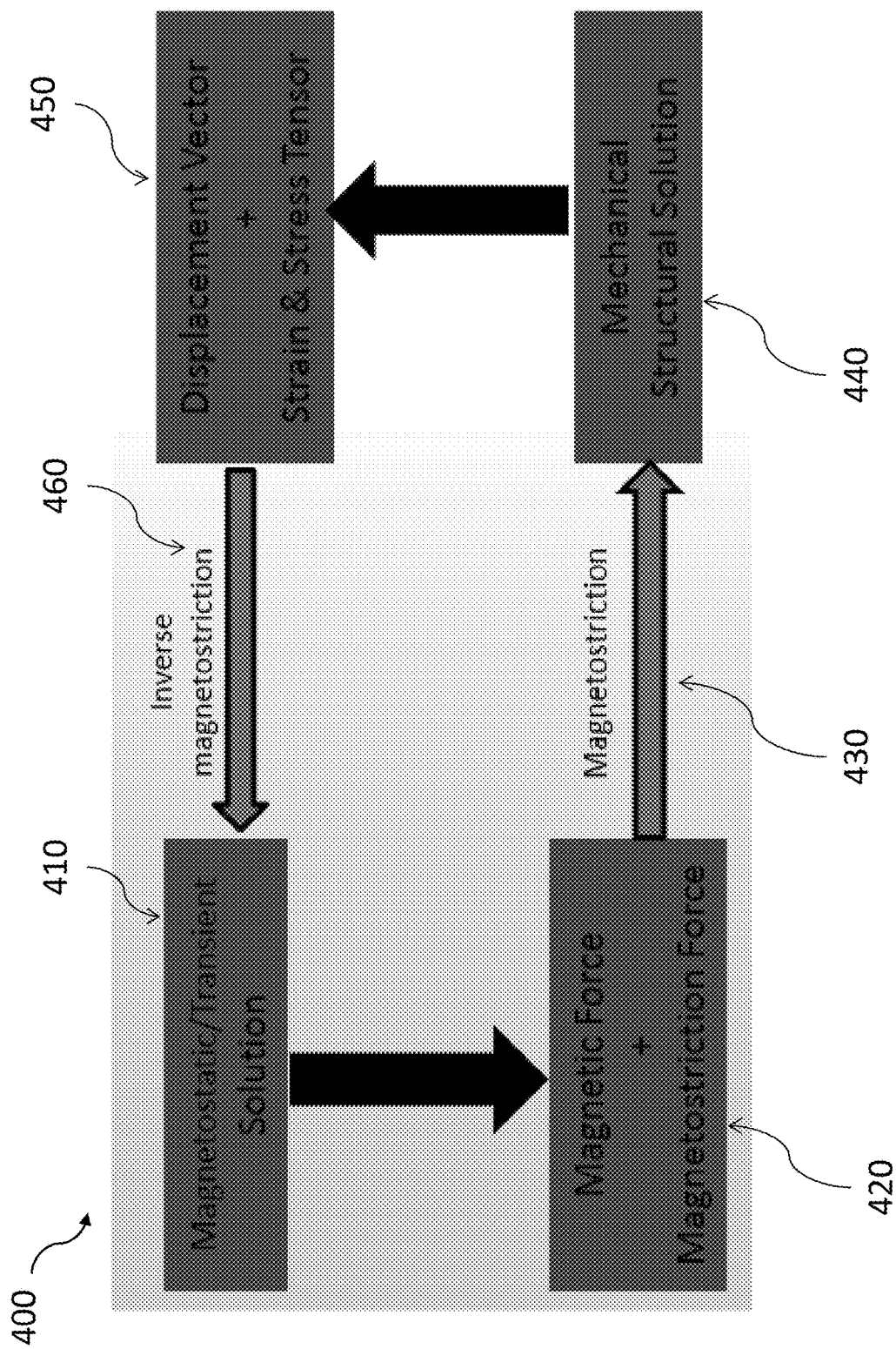
FIG. 4 is a diagram illustrating a sequence of calculations and transformations in a decoupled approach.

FIG. 4 illustrates a process of calculation using a decoupled method 400 according to some variations. In step 410, magnetic equation 310 can be solved using a magnetic mesh. In some variations, equation 410 can be a magnetostatic equation. In some variations, equation 410 can be a magnetotransient equation. In these variations, equation 410 can be solved using a magnetic time constant.

In step 420, results of calculation of step 410 can be used to calculate magnetostriction according to expression 340. In some variations, magnetostriction term can then be mapped to the mechanical mesh in step 430. In some variations, magnetic field can be mapped to the mechanical mesh. In these variations, calculation of magnetostriction can be done on the mechanical mesh.

In step 440, stress equation 320 can be solved using a mechanical mesh. In some variations, displacement vector, strain tensor, and stress tensor can be calculated in step 450. In some variations, the stress equation can be solved in less than six dimensions. In these variations, strain vector and stress vector, or strain scalar and stress scalar, can be calculated instead of strain tensor and stress tensor.

In step 460, inverse magnetostriction can be calculated according to expression 330. Inclusion of inverse magnetostriction changes magnetic equation 310. In some variations, calculation can proceed to step 410 again. In some variations, steps 410, 420, 430, 440, 450, and 460 can be repeated multiple times until a converged solution is obtained. In some variations, only some, but not all, of the steps 410, 420, 430, 440, 450, and 460 can be repeated multiple times.

Figure 5:
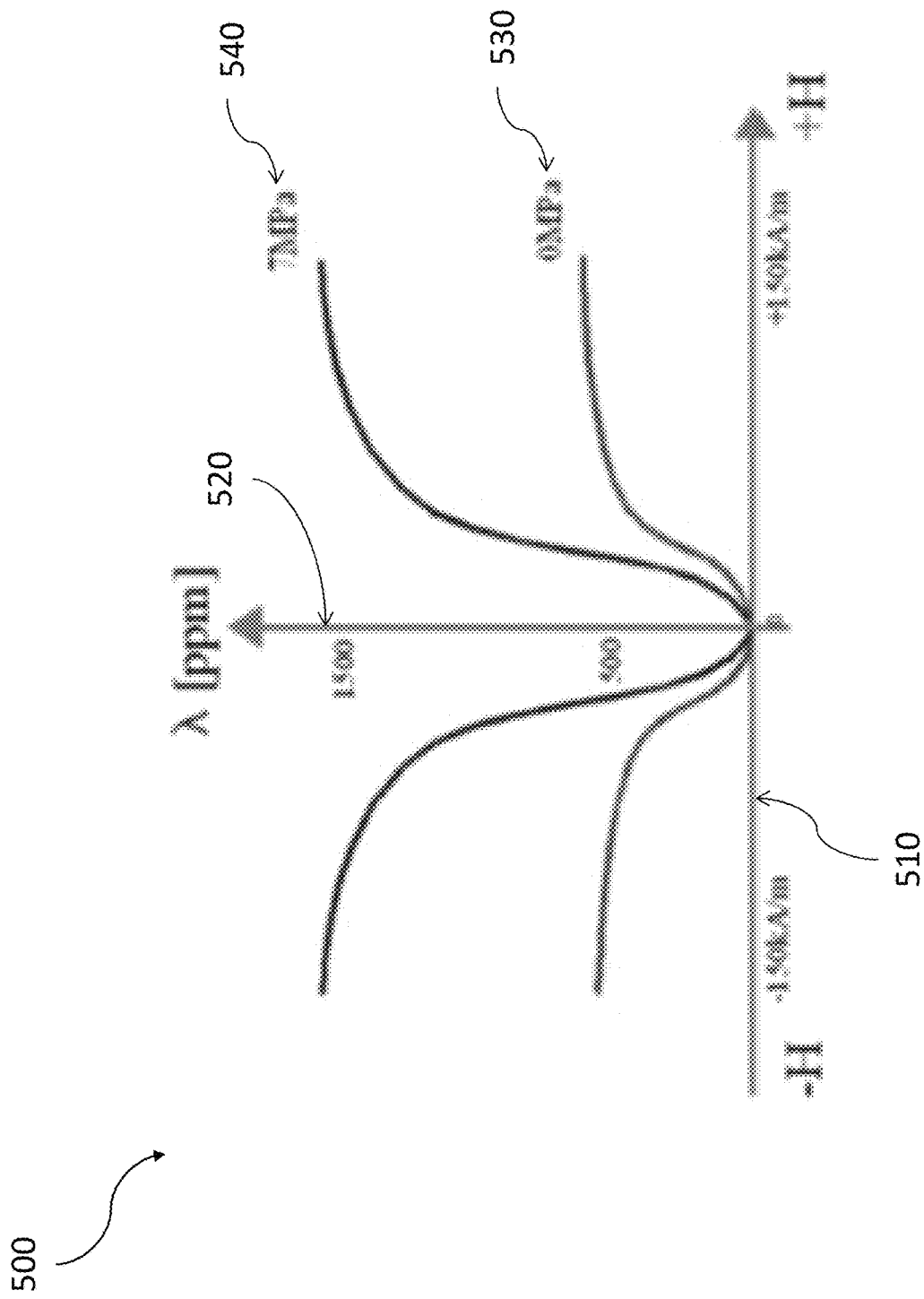
FIG. 5 is a diagram illustrating stress dependent magnetostriction.

The magneto-mechanical coupling coefficients d and $d^T$ can be linear or nonlinear. In some variations, they can also be stress sensitive. An example of such stress sensitivity is illustrated in FIG. 5. Graph 500 shows an example of how magnetostriction λ, plotted along axis 520, can change as a function of magnetic field H, plotted against axis 510. Curves 530 and 540 illustrate how this function can change depending on a pre-stress level. Curve 530 is plotted at zero pre-stress, while curve 540 is plotted at pre-stress of 7 MPa. Different pre-stress can result in different λ-H curves.

Accounting for the stress sensitivity of magnetostriction in a coupled method 200 is not straightforward. In a coupled method, one approach may be to disregard stress sensitivity of the coupling coefficient. This approach can lead to a significant error.

In some variations of a decoupled method 300, the stress field solution can be mapped to the mesh of a magnetic solver. In some variations, the magnetic solver can treat the stress as pre-stress so as to take into account the effect of stress sensitivity. In some variations, the magneto-mechanical coupling coefficient $d^T$ can be expressed as:

$$d^T = f(T) \tag{12}$$

The inverse magnetostriction describes the magnetization change induced by the mechanical loads. The inverse magnetostriction transfers mechanical energy to magnetic energy, so it can be utilized in sensors and energy harvesters. In some variations, magnetic property can be isotropic. In some variations, the nonlinear magnetic property of magnetic material can become anisotropic to take into account the inverse magnetostriction in the magnetic solver. In some variations, the magnetic permeability μ in equation 310 can be written as a tensor:

$$\mu = \begin{bmatrix} \mu_x & 0 & 0 \\ 0 & \mu_y & 0 \\ 0 & 0 & \mu_z \end{bmatrix} \tag{13}$$

and the stress tensor T can be written as:

$$T = \begin{bmatrix} \sigma_x & \tau_{xy} & \tau_{xy} \\ \tau_{yx} & \sigma_y & \tau_{yz} \\ \tau_{zx} & \tau_{zy} & \sigma_z \end{bmatrix} \tag{14}$$

In some variations, for a given unit direction vector x, the normal stress in this direction can be obtained from:

$$\sigma = x^T T x \tag{15}$$

In some variations, normal stress σ can be direction dependent. For nonlinear magnetic material, it may not be feasible to apply an inverse magnetostriction term (the last term in equation 310) during the nonlinear iteration because of the convergence issues. In some variations, the effect of inverse magnetostriction can be taken into account by reconstructing the permeability tensor μ and transforming a problem into a general anisotropic nonlinear magnetic problem. In some variations, this process can follow the process described in: D. Lin, P. Zhou, et al., "A New Nonlinear Anisotropic Model for Soft Magnetic Materials", IEEE TRANSACTIONS ON MAGNETICS, Vol. 42, No. 4, April 2006, which is incorporated here by reference.

When inverse magnetostriction is incorporated in the permeability tensor μ, it means that the original B-H relationship of magnetic material has to be modified. For a given magnetic field H, the induced magnetic flux can be modified as:

$$B = B|_{from\_original\_BHcurve} + d\sigma_H \quad (16)$$

where $\sigma_H$ is the normal stress in direction of H and can be calculated with equation (15).

Then a new B-H relationship in the direction of H can be constructed, and the solution problem becomes anisotropic. The B-H relationship in directions perpendicular to H field obeys the original B-H curve. At a given location, the normal stress is direction dependent, and the direction of H at this location can be adjusted during the nonlinear iterations. It may be not feasible to reconstruct the B-H relationships in the nonlinear iteration process because of the convergence issue. Instead, the B-H relationships can be reconstructed in three orthogonal directions based on the local stress tensor. The problem then becomes a general nonlinear anisotropic problem. With this method, the anisotropic nonlinear property of magnetic material can become predefined locally on each element of the magnetic mesh, there can be no need to reconstruct the B-H relationships at each nonlinear iteration, and inverse magnetostriction effect can be automatically incorporated.

For isotropic material with linear inverse magnetostriction condition with the coupling coefficient d, and the nonlinear B-H curve in the direction of x, y, and z-axis can be reconstructed by:

$$\text{on axis } k \begin{cases} h_i = h_l \\ b_i = b_l + d\sigma_k \end{cases} i = 1, n \ k = x, y, z \quad (17)$$

where n is the total number of discretization points on B-H curve and $\sigma_k$ is the normal stress component of stress tensor T. The original isotropic nonlinear magnetic property can become anisotropic after inverse magnetostriction is applied.

In some variations, inverse magnetostriction can be directional (for example, with magnetostriction and inverse magnetostriction only in the rolling direction). In these variations, it may be convenient to introduce the local coordinate system with the rolling direction as one of the principles axes. In such a case, the normal stress in rolling direction can be calculated by equation (15), and the corresponding nonlinear B-H curves can be reconstructed in a way similar to equation (17).

Figure 6:
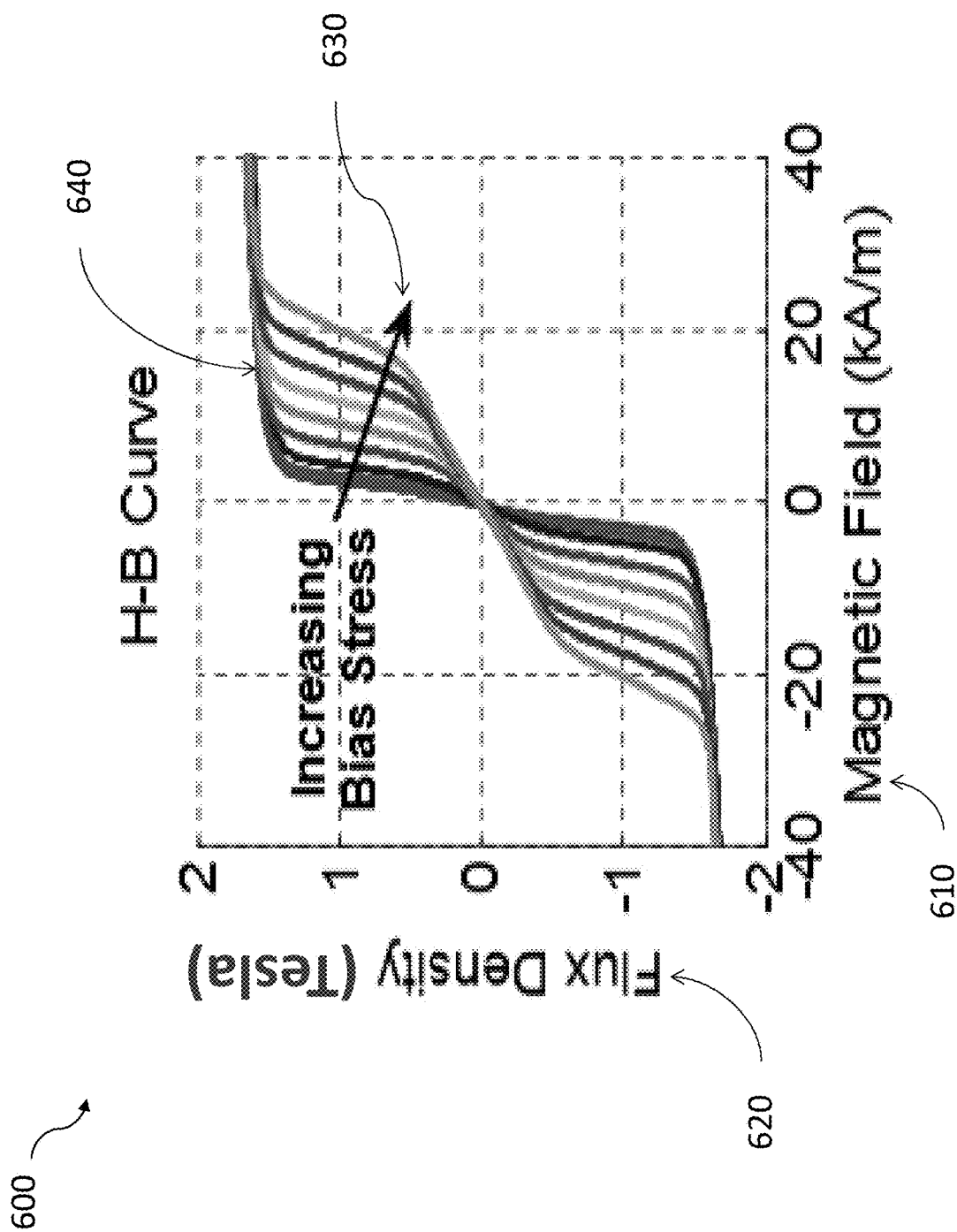
FIG. 6 is a diagram illustrating an approach to accounting for inverse magnetostriction.

FIG. 6 illustrates an example 600 of stress-dependent B-H curves. Flux density B (620) changes as a function of magnetic filed H (610). As bias stress increases (630), the shape of B-H curves 640 can change. The B-H curves 640 can be imported by multiple data sets, and the local coordinate based directional B-H curve can be reconstructed by interpolation. The stress can be calculated from equation (15) and linear interpolation can take place between two neighboring data sets.

By using the reconstruction method, equation 310 can be written as:

$$B = \mu^* H \quad (18)$$

where $\mu^*$ includes the inverse magnetostriction effect:

$$\mu^* = \begin{bmatrix} \mu_x^* & \mu_{xy}^* & \mu_{xz}^* \\ \mu_{yx}^* & \mu_y^* & \mu_{yz}^* \\ \mu_{zx}^* & \mu_{zy}^* & \mu_z^* \end{bmatrix} \quad (19)$$

After such reconstruction, the anisotropic nonlinear magnetic problem can be solved by method described in D. Lin, P. Zhou, et al., "A New Nonlinear Anisotropic Model for Soft Magnetic Materials", IEEE TRANSACTIONS ON MAGNETICS, Vol. 42, No. 4, April 2006, the contents of which are hereby fully incorporated by reference.

Figure 7:
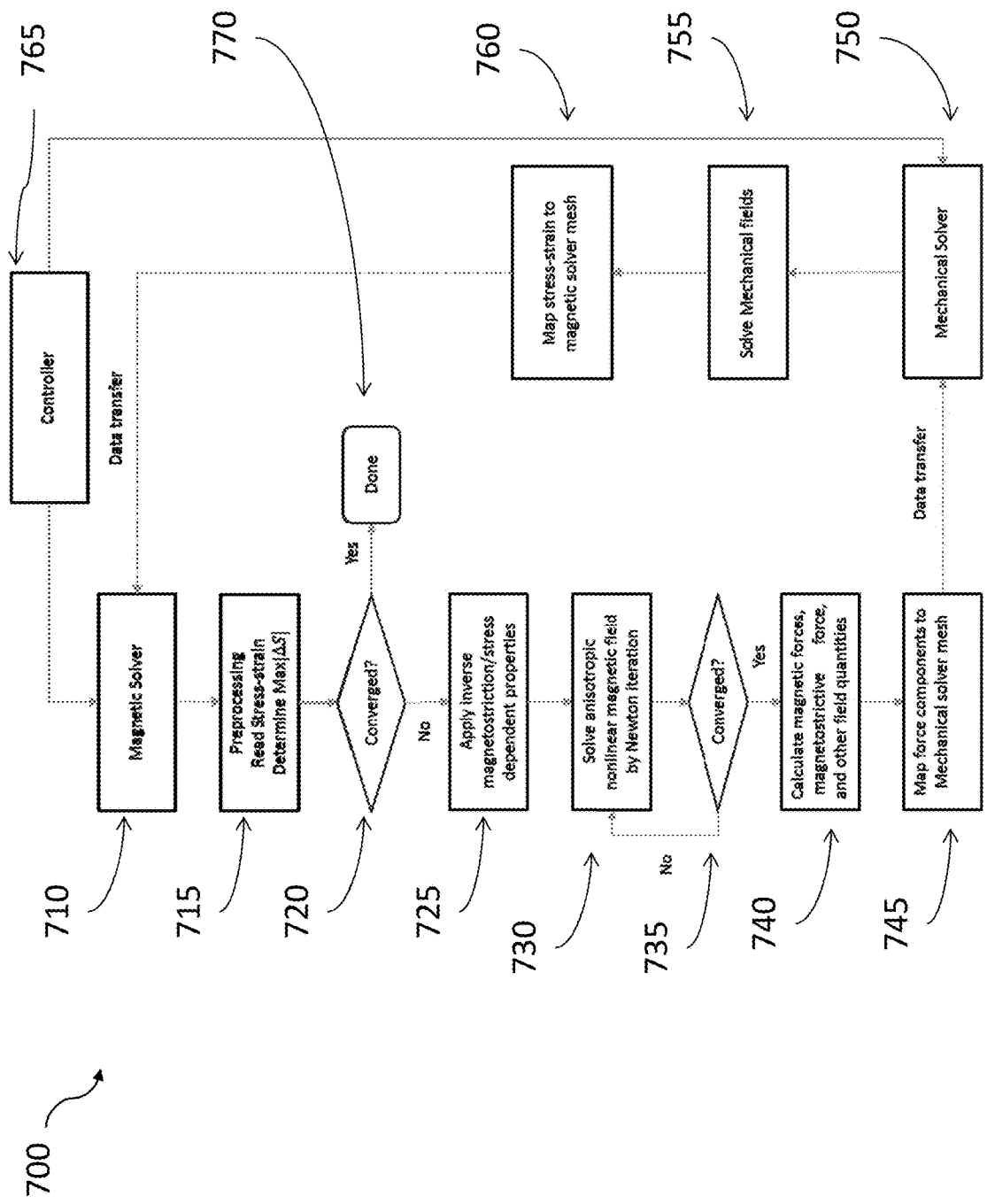
FIG. 7 is a diagram illustrating steps in some variations of a decoupled approach to accounting for magnetostriction and inverse magnetostriction.

FIG. 7 is a diagram illustrating steps in some variations of a decoupled approach to accounting for magnetostriction and inverse magnetostriction. The controller 765 manages the magnetic solver 710 and mechanical solver 750 in the iterative process: the magnetic solver 710 acting as a driver is called first (the pre-stress is assigned to zero by default), and both solvers are called sequentially until the maximum delta deformation is less than the specified convergence criteria.

In some variations, after magnetic solver 710 calculations are completed, preprocessing 715 can include reading stress-strain to determine maximum difference in strain $|\Delta S|$. In some variations, convergence check 720 can follow the determination of maximum difference in strain. In some variations, calculations can terminate (770) after convergence check 720. If convergence check 720 fails, in some variations calculations can proceed to application of inverse magnetostriction stress dependent properties 725. In some variations, process can include solving for magnetic field (730). In some variations, magnetic field can be anisotropic. In some variations, magnetic field can be nonlinear. In some variations, magnetic field can be anisotropic and nonlinear. In some variations, solving for magnetic field can be done by Newton iteration. In some variations, solving for magnetic field can continue until magnetic field solution converges.

After magnetic field solution converges, in some variations process can include calculation of magnetic force, magnetostrictive force, and other field quantities (740). In some variations, force components can be mapped to mechanical mesh (745). In some variations, data can be transferred to mechanical solver 750. In some variations, mechanical solver 750 can solve for mechanical fields 755. In some variations, stress-strain can be mapped to magnetic mesh (760). In some variations, data can be transferred to magnetic solver 710. In some variations, controller 765 can control magnetic solver 710. In some variations, controller 765 can control mechanical solver 750. In some variations, controller 765 can control magnetic solver 710 and mechanical solver 750.

Input data for systems and methods described herein, such as the process of FIG. 7 can be acquired via measurements from a real world apparatus (e.g. a real world transformer) or a model that is based on a real world apparatus (e.g., a model that is based on knowledge acquired based on the structure and behavior of real world transformers). Output data (e.g., a magnetic field solution, magnetic force metrics, magnetostrictive force metrics, field quantities, mechanical field solutions, stress-strain metrics) can be utilized in a variety of downstream manners. In one embodiment, output data are compared to design threshold values to determine whether a system design meets design criteria (e.g., fault tolerances, desirable system behaviors). When the output data indicates a good design, a physical, real world apparatus may be built or adjusted based on an underlying design that resulted in the simulated output data. Such apparatus building or adjustment may be performed by a party that performed a simulation that resulted in generation of the output data, or such building or adjustment may be performed by a third party. In another example, when the output data is deemed acceptable on its own or based on further processing, a system design may be approved for incorporation into a larger system for simulation and system design.

A decoupled method can be used for calculating stress field and magnetic field in various structures, devices, systems. In some variations, the method can be used for noise prediction in transformers. In some variations, the method can be used for electric motor design. In some variations, the method can be applied to design of sensors, actuators, transducers and smart materials.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer-implemented method for rapid calculation of magnetostriction effects comprising:
   receiving data representing a structure, the data comprising a magnetic mesh, a mechanical mesh, and a plurality of material properties;
   calculating, using the received data, a stress field and a magnetic field for the structure by:
      determining a magnetic field on the magnetic mesh;
      determining a magnetostriction from the magnetic field;
      applying the magnetostriction to the mechanical mesh;
      determining a stress field on the mechanical mesh;
      determining an inverse magnetostriction from the stress field;
      applying the inverse magnetostriction to the magnetic mesh;
      determining a new magnetic field on the magnetic mesh by accounting for the inverse magnetostriction; and
   providing data characterizing the calculated stress field and magnetic field for the structure.

2. The method of claim 1, wherein a plurality of material properties comprises a magneto-mechanical coupling coefficient.

3. The method of claim 2, wherein the magneto-mechanical coupling coefficient is dependent on the stress field, and wherein determining the magnetic field comprises:
   mapping the stress field onto the magnetic mesh; and
   treating the stress field as a pre-stress.

4. The method of claim 1, wherein determining the new magnetic field on the magnetic mesh comprises reconstructing of a magnetic permeability to account for the inverse magnetostriction.

5. The method of claim 4, wherein the magnetic permeability is isotropic before reconstructing.

6. The method of claim 4, wherein the magnetic permeability becomes anisotropic after reconstructing.

7. The method of claim 1, wherein the magnetic field and the stress field change with time, wherein determining the magnetic field comprises a calculation with a magnetic time constant, wherein determining the stress field comprises a calculation with a stress time constant, and wherein the magnetic time constant is smaller than the stress time constant.

8. The method of claim 1, further comprising repeating the calculating step until a converged solution is reached.

9. The method of claim 1, wherein operations on the mechanical mesh are performed using a first simulator operating on a first processing system and wherein operations on the magnetic mesh are performed using a second simulator operating on a second processing system.

10. The method of claim 9, wherein the first simulator and the second simulator offer in parallel at some point in time during the method.

11. The method of claim 1, wherein the received data is representative of a physical system that exists or that is being designed.

12. The method of claim 1, wherein the data characterizing the calculated stress field and magnetic field is used to build a component of a physical system or to modify an existing physical component.

13. A computer system to customize software configuration, comprising:
a memory to store data comprising a magnetic mesh, a mechanical mesh, and a plurality of material properties; and
a processor to:
calculate, using the data, a stress field and a magnetic field for the structure by:
determining a magnetic field on the magnetic mesh;
determining a magnetostriction from the magnetic field;
applying the magnetostriction to the mechanical mesh;
determining a stress field on the mechanical mesh;
determining an inverse magnetostriction from the stress field;
applying the inverse magnetostriction to the magnetic mesh;
determining a new magnetic field on the magnetic mesh; and
provide data characterizing the calculated stress field and magnetic field for the structure.

14. The computer system of claim 13, wherein a plurality of material properties comprises a magneto-mechanical coupling coefficient.

15. The computer system of claim 14, wherein the magneto-mechanical coupling coefficient is dependent on the stress field, and wherein the processor maps the stress field onto the magnetic mesh and treats the stress field as a pre-stress.

16. The computer system of claim 13, wherein the processor determines the new magnetic field on the magnetic mesh by reconstructing a magnetic permeability to account for the inverse magnetostriction.

17. The computer system of claim 16, wherein the magnetic permeability is isotropic before reconstructing.

18. The computer system of claim 16, wherein the magnetic permeability becomes anisotropic after reconstructing.

19. The computer system of claim 13, wherein the magnetic field and the stress field change with time, wherein the processor determines the magnetic field by calculation with a magnetic time constant and determines the stress field by calculation with a stress time constant, and wherein the magnetic time constant is smaller than the stress time constant.

20. The computer system of claim 13, where the processor continues to calculate until a converged solution is reached.

21. A computer-implemented method for rapid calculation of magnetostriction effects comprising:
receiving data representing a structure, the data comprising a magnetic mesh, a mechanical mesh, and a plurality of material properties;
calculating, using the received data, a stress field and a magnetic field for the structure by:
applying a determined magnetostriction based on a determined magnetic field to the mechanical mesh;
applying a determined inverse magnetostriction based on a determined stress field to the determined magnetic mesh;
determining a new magnetic field on the magnetic mesh; and
providing data characterizing the calculated stress field and magnetic field for the structure.

22. A computer-implemented method for rapid calculation of magnetostriction effects comprising:
receiving data representing a structure, the data comprising a magnetic mesh, a mechanical mesh, and a plurality of material properties, wherein the magnetic mesh is different from the mechanical mesh and wherein the plurality of material properties comprises an isotropic magnetic permeability, a first magneto-mechanical coupling coefficient, and a second magneto-mechanical coupling coefficient;
calculating, using the received data, a stress field and a magnetic field for the structure by:
determining a magnetic field on the magnetic mesh by solving a magnetic field equation using the isotropic magnetic permeability and a magnetic time constant;
determining a magnetostriction from the magnetic field as a product of the first magneto-mechanical coupling and the magnetic field;
applying the magnetostriction to the mechanical mesh by mapping the magnetostriction from the magnetic mesh to the mechanical mesh;
determining a stress field on the mechanical mesh by solving a strain-stress equation with the magnetostriction using a mechanical time constant, wherein the mechanical time constant is substantially larger than the magnetic time constant;
determining an inverse magnetostriction from the stress field as a product of the second magneto-mechanical coupling and the stress field;
applying the inverse magnetostriction to the magnetic mesh by mapping the inverse magnetostriction from the mechanical mesh to the magnetic mesh;
determining a new magnetic field on the magnetic mesh using the magnetic time constant by mapping the stress field onto the magnetic mesh, treating the stress field as a pre-stress, and reconstructing the isotropic magnetic permeability to account for the inverse magnetostriction such that the reconstructed magnetic permeability is anisotropic;
repeating the calculating until a converged solution is reached; and
providing data from the converged solution characterizing the calculated stress field and magnetic field for the structure.

* * * * *